US010162032B2

(12) United States Patent
Bielmeier et al.

(10) Patent No.: US 10,162,032 B2
(45) Date of Patent: Dec. 25, 2018

(54) MAGNETIC RESONANCE APPARATUS AND OPERATING METHOD

(71) Applicant: Siemens Aktiengesellschaft, Munich (DE)

(72) Inventors: Wolfgang Bielmeier, Erlangen (DE); Miriam Keil, Erlangen-Dechsendorf (DE); Joerg Roland, Hemhofen (DE); Stephan Stoecker, Baiersdorf (DE)

(73) Assignee: Siemens Aktiengesellshaft, Munich (DE)

( * ) Notice: Subject to any disclaimer, the term of this patent is extended or adjusted under 35 U.S.C. 154(b) by 632 days.

(21) Appl. No.: 14/854,451

(22) Filed: Sep. 15, 2015

(65) Prior Publication Data

US 2016/0077181 A1    Mar. 17, 2016

(30) Foreign Application Priority Data

Sep. 16, 2014  (DE) ........................ 10 2014 218 530

(51) Int. Cl.
| | |
|---|---|
| *G01R 33/561* | (2006.01) |
| *G01R 33/54* | (2006.01) |
| *A61B 5/055* | (2006.01) |
| *G01R 33/28* | (2006.01) |
| *G01R 33/48* | (2006.01) |

(52) U.S. Cl.
CPC ............ *G01R 33/543* (2013.01); *A61B 5/055* (2013.01); *G01R 33/288* (2013.01); *G01R 33/4806* (2013.01)

(58) Field of Classification Search
CPC .. A61B 5/055; G01R 33/288; G01R 33/4806; G01R 33/543
See application file for complete search history.

(56) References Cited

U.S. PATENT DOCUMENTS

| | | | |
|---|---|---|---|
| 2003/0080738 A1 | 5/2003 | Brinker et al. | |
| 2005/0197077 A1* | 9/2005 | Bielmeier ............ | G01R 33/543 455/115.1 |
| 2006/0158185 A1* | 7/2006 | Kruger ............... | G01R 33/4824 324/307 |
| 2009/0289631 A1 | 11/2009 | Van Den Brink et al. | |

(Continued)

OTHER PUBLICATIONS

Nazarian et al; "Feasibility of Real-Time Magnetic Resonance Imaging for Catheter Guidance in Electrophysiology Studies"; Circulation; vol. 118; pp. 223-229;( 2008).

*Primary Examiner* — Jay Patidar

(74) *Attorney, Agent, or Firm* — Schiff Hardin LLP

(57) ABSTRACT

In a magnetic resonance apparatus and an operating method therefor in which magnetic resonance data are acquired from a patient, a measurement process is used in which a number of magnetic resonance sequences are carried out sequentially, and a maximum measurement time parameter, describing a maximum possible measurement time for undershooting a threshold value for the overall energy input into the patient during the measurement process, is established, taking into account other known recording parameters of the measurement process. The maximum measurement time parameter is used to restrict the ability of an operator to set a measurement time parameter describing the measurement time as a recording parameter, and/or is used as the measurement time parameter.

17 Claims, 2 Drawing Sheets

(56) References Cited

U.S. PATENT DOCUMENTS

| | | | |
|---|---|---|---|
| 2010/0090694 A1* | 4/2010 | Heid | A61B 5/055 324/309 |
| 2013/0090776 A1* | 4/2013 | Feiweier | A61B 6/586 700/295 |
| 2017/0082710 A1* | 3/2017 | Zeller | A61B 5/055 |

* cited by examiner

MAGNETIC RESONANCE APPARATUS AND OPERATING METHOD

BACKGROUND OF THE INVENTION

Field of the Invention

The present invention concerns a method for operating a magnetic resonance apparatus for recording (acquiring) magnetic resonance data of a patient, wherein a measurement procedure is used in which a number of magnetic resonance sequences, which may be identical, are executed sequentially. The invention also concerns a magnetic resonance apparatus and a non-transitory, computer-readable storage medium encoded with programming instructions for implementing such a method.

Description of the Prior Art

Magnetic resonance apparatuses are widely known and used. In medical imaging, nuclear spins of a patient are aligned in a basic magnetic field and excited by radio-frequency pulses, so that their decay signal can be measured. Gradients are superimposed on the basic magnetic field in order to assign spatial information to the measured magnetic resonance signals.

With the radio-frequency pulses, energy is imparted into the patient, and some of this radio-frequency energy is absorbed and can lead to heating of tissue. Thus safety monitoring in magnetic resonance scanners is common, and energy monitoring represents an important part of this safety monitoring. Such energy monitoring is designed to ensure that tissue is not heated to an unacceptable extent in the magnetic resonance scanner. Therefore, a check is made within the magnetic resonance apparatus, for example by a suitable control device, as to whether, within the framework of a measurement process, at least one predetermined threshold value for the energy imparted into the patient, specified in Joule/Kilogram for example, is being exceeded. This energy monitoring is undertaken by predicting the amount of energy for the intended measurement, for example as part of the preparation of the magnetic resonance sequence, as well as by monitoring the absorbed energy during the measurement process (online monitoring).

Exceeding the threshold value in the preparation of the sequence or during the execution of the measurement process leads to the magnetic resonance measurement being aborted. In such cases, legally-defined threshold values, for example 14,400 Joule/Kilogram can be used as the threshold, but often further manufacturer-specific threshold values, below the legal threshold value, are monitored, which are intended to serve as a warning. If the threshold value serving as the warning is exceeded, a pop-up and/or another message can appear at the operating interface of the magnetic resonance device, which indicates to the operator that the threshold value is about to be exceeded. If this occurs in the sequence preparation, the sequence can still be started by confirming the measurement process, but exceeding the threshold during the measurement process can lead to the measurement process being aborted. A threshold value serving as a warning can be, for example, 6,000 Joule/Kilogram.

The aforementioned threshold values are not reached by many measurement processes that are usually undertaken, even if the processes include multiple sequential executions of magnetic resonance sequences, but problems occur when longer measurement processes are specified in which multiple magnetic resonance sequences are employed sequentially in order to record the magnetic resonance data. An example of this type of process is the type of measurement processes used to monitor a minimally-invasive intervention with the magnetic resonance apparatus, in which, with a specific magnetic resonance sequence or a specific series of magnetic resonance sequences, an imaging area, for example a specific slice, is recorded and displayed continuously for the generation of monitoring images. Examples for such minimally-invasive interventions that are possible under magnetic resonance guidance are biopsies, the positioning of catheters, and the like. By contrast, in diagnostic measurement processes for imaging in order to monitor an intervention at the patient, a continuous updating of the magnetic resonance data is needed. Such continuously performed measurement processes are frequently also interactive, meaning that it is possible to change recording (data acquisition) parameters during the measurement process, for example to adapt a slice to be recorded, or the like.

In order to simplify the workflow for such measurement processes, typically the number of individual measurements to be carried out with magnetic resonance sequences is set to a maximum, the measurement process is started and it is aborted when imaging monitoring is no longer needed. This produces very long "virtual" measurement times, but such measurement that typically are not fully utilized. Frequently an "unlimited measurement time" option is also offered at an operator interface of the magnetic resonance device in order to initiate a continuous measurement process of unknown length.

In this type of operation of many devices for energy monitoring of magnetic resonance apparatuses, it is now established that a limit value for the energy imparted into the patient could be exceeded, so that starting a measurement process is avoided. It is precisely when a lower threshold value serves as a warning that a warning occurs for a majority of these interactive measurement protocols, which makes an acceptable workflow for this application at the magnetic resonance apparatus difficult to impossible.

This is because in the known implementations, the maximum measurements that is able to be used must be reduced manually, often by trial and error, so that the threshold value for the energy input is no longer exceeded. This is a major drawback since the energy input depends on the respective settings of the recording parameters (flip angle, saturation setting, sequence timing etc.). This leads to a complex, manual optimization of a measurement time, which in most cases is just not needed. If generic, maximum allowed values are used as the starting point, these must be valid for all possible measurement protocols (measurement processes) which leads to significant, unnecessary restrictions for individual measurement processes.

This problem arises especially markedly during the described adaptation of recording parameters during the measurement process. Many recording parameters, for example the selection of a slice, have an effect on the actual energy input into the patient, so that a change of a recording parameter related to the slice, for example, can lead to the threshold value being exceeded that is still being determined subsequently for the other given recording parameters, and the measurement then being aborted. This can be problematic, especially when carrying out a minimally-invasive intervention.

SUMMARY OF THE INVENTION

An object of the present invention is to provide an improved setting of the magnetic resonance apparatus during measurement processes in which a number of magnetic resonance sequences and/or the same magnetic resonance sequence are used sequentially.

This object is achieved by a method of the type described initially, but wherein, in accordance with the invention, a maximum measurement time parameter is programmed into the control computer with which an operator interfaces to set recording parameters for an MR examination procedure, the maximum time parameter establishing a maximum possible measurement time that still permits a threshold value for the overall energy imparted into the patient during the measurement process not to be exceeded, taking into account other known recording parameters of the measurement process. The maximum measurement time parameter automatically limits the ability of the operator to set the measurement time parameter describing the measurement time as a recording parameter and/or as the measurement time parameter in the MR examination procedure.

In accordance with the present invention, from the recording parameters of the measurement process (and naturally the system parameters permanently specified for the magnetic resonance apparatus), the control computer automatically calculates how many individual measurements would be possible with one magnetic resonance sequence in each case without exceeding the threshold value for the input of energy into the patient. Thus a maximum allowable measurement time is determined as a maximum measurement time parameter on the basis of a restriction of the energy input. The maximum measurement time parameter can be, for example a maximum possible measurement duration and/or a maximum possible number of individual measurements with a magnetic resonance sequence. The maximum measurement time parameter can in its way already correspond to another recording parameter, namely the measurement time parameter, so that the calculated maximum measuring time parameter can directly be set automatically as the measuring time parameter, which is especially expedient for measurement processes for which the measurement time is not fixed in any event in advance. Moreover, the maximum measuring time parameter can also be used to limit the setting options for an operator so that thus a dynamic adaptation of the restriction as a function of the current recording parameters of another type can be achieved.

As has already been noted, the present invention offers improvements particularly for measuring processes in which the measurement time is not defined in advance, i.e. for measurement processes that serve a monitoring function. Thus the measurement process may contain a repeated measurement in the same recording region with the same magnetic resonance sequence, meaning that cyclically, after specific time intervals, current magnetic resonance data of a recording region are recorded (acquired) with the same magnetic resonance sequence, so that the monitoring function can be realized. The measurement process can be implemented so as to guide a minimally-invasive intervention at the patient, even if the duration thereof is unknown in advance, and the inventive method in such cases allows the maximum possible measurement time with respect to the threshold value measurement process to be determined specifically as a function of the currently set recording parameters, and if necessary even to define it automatically so that the workflow is greatly simplified.

The inventive method naturally can also be applied to other measurement processes in which a number of consecutive individual measurements with the same or different magnetic resonance sequences are implemented, for example within the framework of functional magnetic resonance imaging and/or for use of EPI-BOLD methods and the like.

It is expedient for the maximum measurement time parameter and/or the measurement time parameter to be displayed, especially during the measurement process. This is particularly meaningful when the maximum measurement time parameter is used for automatic setting of the corresponding measurement time parameter, since then it is possible to appropriately inform a person carrying out the intervention. For example, the maximum measurement time still remaining during imaging monitoring of an intervention can be constantly shown updated on a status screen, with this information being continually updated even during changes to recording parameters, for example recording parameters defining the slice location. For example, if the operator selects an unrestricted, meaning a longest possible, duration of the measurement process, it is thus possible, for any changes of recording parameters that occur in the course of the interactive measurement process that have an influence on the maximum possible measurement time, to calculate these parameters and also to update the corresponding recording parameters of the measurement protocol automatically, so that a warning and/or an abortion of the measurement process is avoided.

As noted, in a preferred embodiment of the invention in which an unrestricted duration of measurement process is selected by an operator, the maximum measurement time parameter is set directly as the measurement time parameter. The operator is thus provided with the option of not specifying any actual requirement for the duration of the measurement process, for example a number of repetitions of the measurement sequence, but instead to leave this open. Especially for image monitoring of an intervention, this is an extremely useful setting. The operator then does not have to worry about anything else in relation to the measurement time, since the maximum measurement time parameter is always defined and set on the basis of the current recording parameters, so that during the checking/execution of the measurement process, reaching the threshold value is avoided in advance and disruptive pop-ups, messages, measurement abortions and the like are prevented. Through this automatic maximization of the number of individual measurements, an extremely simple workflow is produced without a maximum value for all measurement protocols (measuring processes) having to be set to a minimum of the allowed values.

In a further embodiment of the invention, the threshold value serves only as a warning, and exceeding the threshold value is made possible after an action by the operator and a warning is issued that the threshold value has been exceeded. When the threshold value only involves a value that serves as a warning so that when the exceeded value does not yet, for example, contravene legal requirements, the operator can be given the opportunity of explicitly exceeding the threshold. In such cases, the operator should of course be given sufficient information about the threshold being exceeded, so there is an indication warning that the threshold is being exceeded, for example by a pop-up or another type of window that contains a corresponding warning message. It is also useful in this context to use multiple thresholds, so that after a first threshold value serving as a warning has been exceeded, a higher second, absolute threshold is established, in order to establish a new maximum measurement time parameter. Thus a type of graduation of threshold values can be implemented with the first threshold value, serving as the initial warning, being taken into consideration to determine the second threshold. If the user specifies that this first threshold value should be deliberately exceeded, it is still possible to continue to carry out the method, but now a higher, second absolute threshold value is used as the threshold value that is to be taken into consideration when establishing the maximum measurement time parameter, for example a legally specified threshold value, so that the inventive method can still be employed in order to avoid the second, absolute threshold value from being exceeded. In this case it should be noted that a threshold value serving as a warning is not absolutely necessary; naturally the method is also able to be used when working directly with an absolute threshold value, which may also not be exceeded after a manual entry by an operator.

Preferably with a change of recording parameters during the measurement process, an energy input into the patient that has already occurred is taken into account by the already concluded part of the measurement process during the determination of the updated maximum measurement time parameter. This means, for calculating how many individual measurements are still possible without exceeding that the threshold value, the energy dose already absorbed by the patient can be taken into account, which means that portions of the measurement process already executed also continue to be taken into account. For determining the energy input into the patient that has already occurred, a calculation algorithm can be used that was previously used for the determination of the maximum measurement time parameter, for example a worst-case estimation. It is also possible, however, to refine the energy input into the patient already undertaken partly by measurement data, wherein for example characteristics of the patient known in the interim and/or a relationship between flip angle and transmitter voltage becoming known within the framework of a sequence preparation can be taken into account in order to make possible an improved calculation of the energy input already undertaken.

To establish the maximum measurement time parameter, the energy inputs into the patient by radio-frequency pulses of the magnetic resonance sequences can be established, summed and compared to the threshold value. Magnetic resonance sequences, as is widely known, use radio-frequency pulses, for example excitation pulses, refocusing pulses, inversion pulses and the like, which are primarily responsible for the energy input into the patient. This specific embodiment of the present invention thus allows the energy inputs that occur through the radio-frequency pulses of the magnetic resonance sequences to be individually determined, so that they can be summed and compared with the threshold value. As soon as the threshold value is reached or exceeded, it is clear that the maximum possible measurement time has been reached without exceeding the threshold value (at least in this estimation).

In order to establish the energy input produced by a radio-frequency pulse, the flip angle to be created by the radio-frequency pulse, and a relationship between the transmitter voltage and the flip angle created in the patient, are used. This relationship is established by a prior measurement or from a worst-case assumption. Before a measurement is actually undertaken, it is usually not known which RF transmitter voltage is needed in order to achieve a specific flip angle. In the so-called sequence preparation at the beginning of a measurement process and/or before carrying out a measurement sequence, it can be established, for example, which transmitter voltage is needed to achieve a flip angle of 90°, from which transmitter voltages for other flip angles can also be derived. However it is ultimately the transmitter voltage that describes the energy actually transmitted with the radio-frequency pulse, and thus reflects the basic "input energy" available, that acts on the patient for absorption. In order to obtain, through an estimation or establishment, the energy made available by the radio-frequency pulse already at a point in time at which the recording parameters are set, and ideally also the point in time at which the maximum measurement time parameter is to be determined, there are essentially two options available. The measurement can be made in advance as a prior measurement, with which the relationship between transmitter voltage and flip angle is defined, but this is less preferred since an additional measurement operation is then required. It is therefore more useful to make worst-case estimation. In this estimation, transmitter voltages for at least one of flip angle needed in the past can be stored and the maximum of these values is always employed. It is also possible to derive a worst-case assumption from the known specifications of the magnetic resonance device. Using a worst-case assumption, it is actually possible for the maximum possible measurement time to be estimated shorter than it would be in reality, which is an acceptable restriction for complying with threshold values related to the safety of the patient.

With the known transmitter voltages and the flip angles to be created it is thus possible to establish the energy that is available for absorption in the patient. In order to establish the actual desired absorption, i.e. the energy input, a calculation can be made from the emitted energy calculated with the transmitter voltage for the flip angle of the radio-frequency pulse, to determine the energy input in the patient on the basis of an absorption value, for example an absorption factor lying between 0 and 1, which relates to the absorption characteristics of the tissue in the patient. Establishing such an absorption value is a task which is based on more complex physical observations. For this purpose, there are a number of variants, possibly also usable in combination. For example, the absorption value can be read out of the characteristic field and/or can be determined taking into account at least one item of patient data and/or taking into account a worst-case assumption and/or taking into account a tissue absorption model. The absorbed energy, i.e. the energy input, is dependent on different information about the tissue structure of the patient, for example characteristics relating to the fat content, the water content and the salts occurring in the patient. Here as well a worst-case assumption can thus be made that assumes a conceivably unfavorable constellation in the tissue, in order to then especially determine the absorption value for all patients. A calculation within the framework of the tissue absorption model is possible, with which, for example, a simulation can be carried out in order to determine the actual absorption. If data about the current patient, i.e. patient data, are not included, a characteristic graph, precisely for worst-case assumptions, can be stored in the magnetic resonance apparatus, which can be accessed as part of the inventive method, in order to establish the energy input as a function of the energy emitted and thus available for absorption. Naturally it is also conceivable to expand such characteristic graphs to characteristic fields that are additionally dependent on specific patient data, for example on the gender of the patient and/or on the age of the patient and/or on the weight of the patient and the like. Naturally, depending on available resources, different levels of accuracy can be used, wherein in general data also obtained with the magnetic resonance device itself can be understood as patient data, for example data obtained by a localizer about the tissue structure and the like.

As noted, it is especially useful for the establishment of the maximum energy value to be undertaken after each updating of a recording parameter included in the establishment. This can be done within the framework of a sequence check. Operating devices for magnetic resonance devices, especially operator interfaces, usually provide the opportunity to set different recording parameters for the following measurement process for magnetic resonance sequences of the individual measurements. If one of these recording parameters is changed, especially by the operator, routines are known for checking the permissibility of the other recording parameters, which can be referred to as a whole as a measurement protocol for the measurement process, based on the interaction of the changed parameter with the other parameters and the interaction of all parameters with each other. In this case there are complex relationships between groups of recording parameters, which are taken into account such known methods. A few parameters, after they are included in the establishment of the maximum measurement time parameter, now have an influence on the maximum possible measurement time with a measurement protocol for complying with the threshold value, so that the process for updating the maximum measurement time parameter can be integrated without a problem into the overall concept.

The invention also concerns a magnetic resonance apparatus having a control computer configured to implement the inventive method. In particular a processor or computing stage for establishing the maximum measurement time parameters can thus be provided as a part of the control computer, for example as a subcomponent and/or in a close cooperation with an input unit (interface), via which recording parameters are set as a measurement protocol for a measurement process by the control console of the magnetic resonance apparatus. All of the above statements in relation to the inventive method apply analogously to the inventive magnetic resonance apparatus, with which the advantages already stated can thus also be obtained.

[TAPE] Such a storage medium can be, for example, a CD-ROM or the like. The statements above also apply to the storage medium.

DESCRIPTION OF THE PREFERRED EMBODIMENTS

Figure 1:
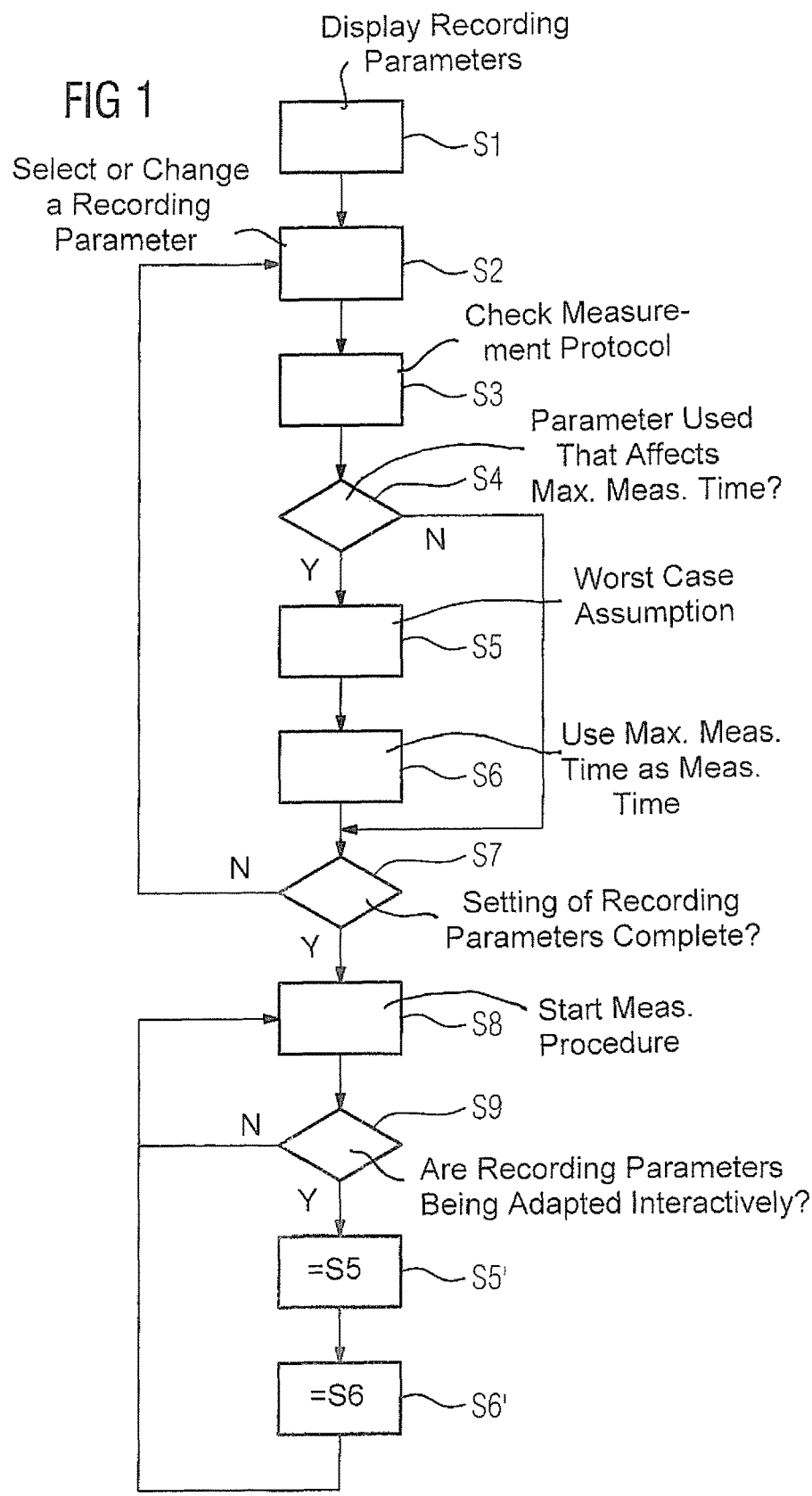
FIG. 1 is a flowchart of an exemplary embodiment of the inventive method.

The exemplary embodiment of the inventive method now shown is integrated into the setting operation of a magnetic resonance device. In this case some of the steps shown here relate to the setting of the magnetic resonance device per se. This involves the setting of a magnetic resonance device, thus the definition of recording parameters, which in their totality can be referred to as a measurement protocol, for a measurement process in which the same magnetic resonance sequences are repeated in order to make possible an image monitoring of a recording region in a patient. The measurement process can be interactive, meaning that it should be possible, while the measurement sequence is also running, to continue to change recording parameters, for example the slice positioning. In this case threshold values are to be complied with, namely on the one hand a threshold value serving as a warning for the energy input into the patient by the measurement process, which is lower than a second, absolute threshold value for the energy input into the patient, which should not be exceeded in any event, on the other hand said second threshold value.

In step S1, before the beginning of the measurement process, the setting of the recording parameters is started. To this end an operator interface is displayed to an operator on an operating device of the magnetic resonance device, in which different recording parameters are able to be selected. In particular the operator interface has an option of measurement unrestricted in time activated by default for image monitoring, meaning that the operator does not yet know, since an image monitoring of an intervention is to take place, how long the measurement is actually to last and would like to know the maximum available measurement type set as part of the threshold values so that a premature interruption of the measurement process cannot result from an incorrectly preselected measurement time. It is assumed below that this option is activated; if it is deactivated it is still possible, as described below, to establish a maximum measurement time parameter, which then however applies as the upper boundary for the measurement time parameters now able to be set for the measurement time and is applied in the operator interface.

In step S2, a recording parameter is now changed or selected by an operator. This leads, in a step S3, to the measurement protocol being checked, as is basically known, which means that a check is made as to whether the set recording parameters will lead to sensible, realizable magnetic resonance sequences in the individual measurements. As part of this checking, a check is also made in a step S4 as to whether a recording parameter was used or set which has influence on the maximum possible measurement time for undershooting the threshold value for the energy input into the patient. If this is the case, in a step S5, a maximum measurement time parameter is determined. The maximum measurement time parameter describes the maximum possible measurement time until there is a threat of the threshold value being exceeded. It is produced in the present case by determining the individual energy inputs of individual radio-frequency pulses of the magnetic resonance sequences used in the measurement process which can be summed in their chronological sequence, so that by a comparison with the threshold value it can be established whether these are being exceeded. Thus the maximum measurement time parameter is easily produced, which for example can contain a number of possible individual measurements with magnetic resonance sequences and/or a measurement time per se, for example in minutes.

In order to determine the energy input of an individual radio-frequency pulse, the flip angle to be achieved must be known and the transmitter voltage which is necessary for achieving said angle. The transmitter voltage is usually only determined at the beginning of an actual measurement, thus of the measurement process, in a prior measurements, for example for a flip angle of 90°, wherein the transmitter voltage for other flip angles is then produced. Therefore at this point, in step S5, a worst-case assumption for the required transmitter voltage is still made, which can be produced for example from statistical observations of the past and/or physical characteristics of the magnetic resonance device. For example this can involve a type of "default value" for a specific flip angle. In alternatives it is basically also possible to have already undertaken a prior measurement here. The transmitter voltage to achieve the desired flip angle with the radio-frequency pulse specifies the energy which is actually to be emitted, thus is available within the patient for absorption. The energy actually absorbed in the patient, i.e. the energy input, is produced in the present case via an absorption value, in concrete terms an absorption factor lying between 0 and 1, by which the emitted energy is multiplied and which can be retrieved depending on patient data from a characteristic field. The characteristic field has been determined on the basis of a tissue absorption model as part of the simulation, in which in turn worst-case assumptions for tissue characteristics not directly able to be derived from patient data are included.

The corresponding energy doses for the individual measurements and thus also the number of individual measurements before the threshold value is reached are produced from these energy inputs, at least in a good estimation, which on the basis of the worst-case assumptions does not conceal any risk of the value still being exceeded. It should be noted again that a direct relationship of course exists between the number of individual measurements and the measurement time arising, which is produced from a known duration for the individual measurements, namely the repetition time.

In step S6, the maximum measurement time parameter as a result of the activated option discussed above of the basically unrestricted measurement is used directly as a corresponding measurement time parameter of the recording parameters and is also displayed in the operator interface. Thus the operator is also informed about the maximum possible measurement time.

It should be noted again that the first threshold value serving as a warning can also be deliberately exceeded by an operator, for example via a corresponding operating element. Then a clear warning message, for example in the form of a pop-up, appears but the method is still continued however, only that now the second, higher, absolute threshold value is used for which no option of deliberately exceeding said value exists.

In step S7, a check is made as to whether the setting of the recording parameters is completed or not. If it is not, the process is continued again with step S2. Otherwise the measurement process is started in step S8 and carried out. During the measurement a check is made in step S9 as to whether recording parameters are being adapted interactively. If this is not the case, the execution of the measurement process is continued in step S8. If, however, a change of a recording parameter occurs which also influences the maximum possible measurement time for complying with the threshold value for the energy input into the patient, in the steps S5' and S6', which correspond to the steps S5 and S6, the calculation to establish an updated maximum measuring time parameter and for setting the current measurement time parameter is undertaken again. Naturally the display is also further updated, which in any event can also occur during the measurement as for example remaining measurement time.

Figure 2:
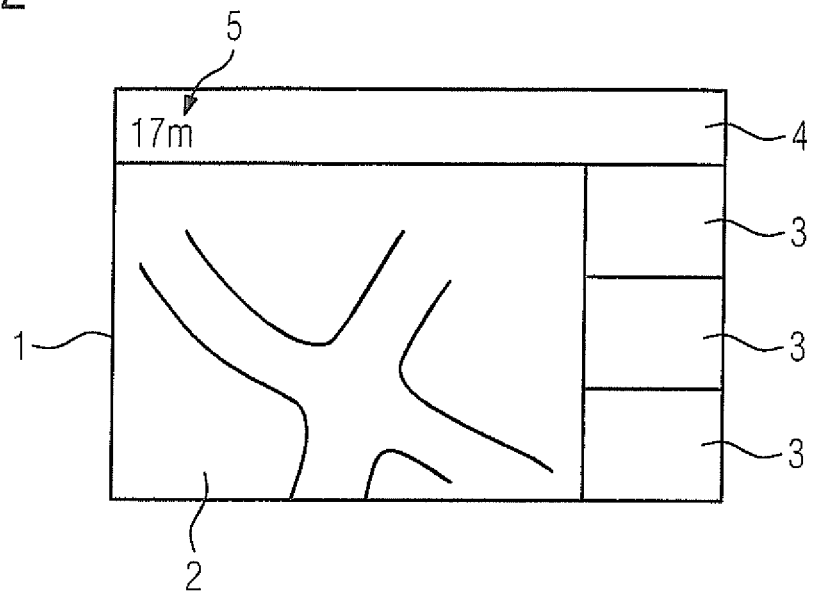
FIG. 2 shows an example of status display of a magnetic resonance apparatus in accordance with the invention.

A corresponding system 1 is shown schematically in FIG. 2. The operator interface there can be displayed during the image monitoring and contains an area 2 for showing current magnetic resonance data, operator elements 3 as well as a status line 4 in which, in the present example, the maximum possible measurement time 5 still remaining is displayed constantly updated.

It should be noted again that in the steps S5' and S6' naturally the energy input already irradiated into the patient during the measurement process already carried out is taken into account, wherein now measured parameters can also be included there for more precise establishment, for example the transmitter voltage which is needed for a specific flip angle.

Figure 3:
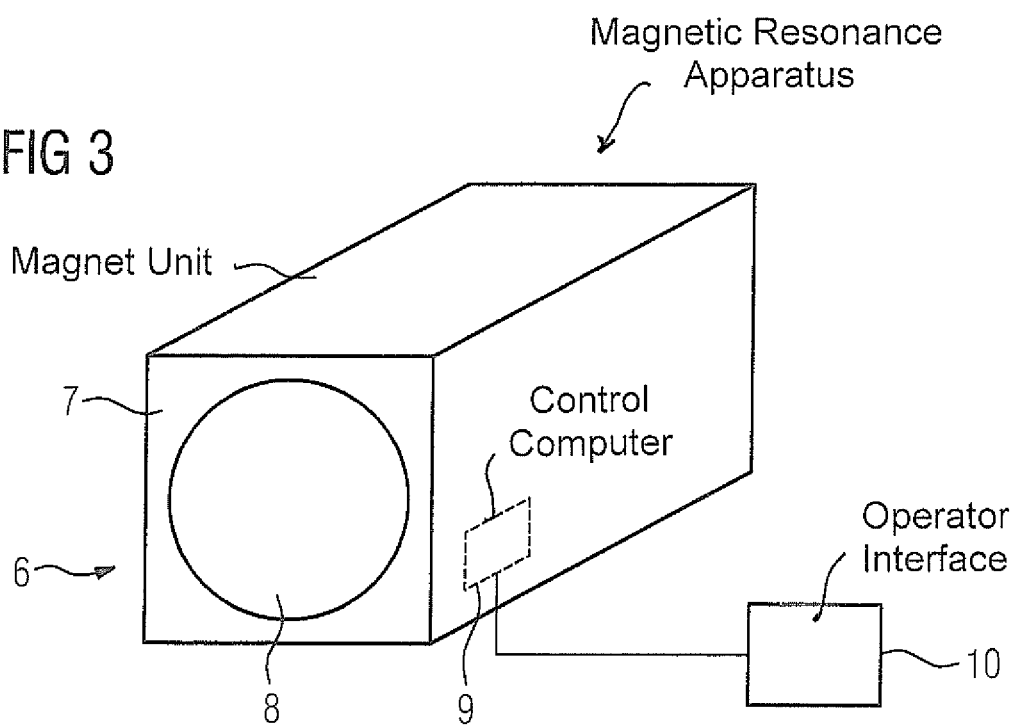
FIG. 3 schematically illustrates an inventive magnetic resonance apparatus.

FIG. 3 shows a basic illustration of an inventive magnetic resonance apparatus 6. As is known, this has a basic magnet unit 7 forming a scanner, which defines a patient receiving area 8 into which the patient can be moved by a patient bed (not shown). Surrounding the patient receiving area 8, as is also known and thus not shown for clarity, a radio-frequency coil arrangement and a gradient coil arrangement are provided. The operation of the scanner is controlled by a control computer 9, which is configured to cause the inventive method to be implemented, and to this end, for example, communicates with an operator interface 10, possibly situated remotely from the scanner.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating a magnetic resonance apparatus to acquire magnetic resonance data from a patient, comprising:
    generating control signals in a control computer in order to operate a magnetic resonance scanner, while a patient is situated therein, to execute a magnetic resonance data acquisition procedure comprising a plurality of individual magnetic resonance sequences that are executed sequentially;
    in said control computer, establishing a maximum human time parameter that designates a maximum of a measurement time for sequentially executing at least some of said magnetic resonance sequences in said plurality of magnetic sequences, before a threshold value is exceeded that designates an overall energy input into the patient during said magnetic resonance data acquisition procedure, said control computer establishing said maximum measurement time parameter dependent on predetermined recording parameters for said magnetic resonance data acquisition procedure; and
    at an input interface of said control computer, when an operator makes manual entries of at least some of said recording parameters that do not restrict said measurement time, automatically limiting a designation of said measurement time at said input interface to said maximum measurement time parameter, and generating control signals in said control computer representing said magnetic resonance data acquisition procedure with said measurement time limited to said maximum, in a form for forwarding to said magnetic resonance scanner.

2. A method as claimed in claim 1 wherein said magnetic resonance sequences in said plurality of magnetic resonance sequences are all identical.

3. A method as claimed in claim 1 comprising, in said measurement procedure, making repeated magnetic resonance data acquisition of a same recording region with a same magnetic resonance sequence in said patient.

4. A method as claimed in claim 1 comprising executing said measurement procedure as guidance for a minimally-invasive intervention of said patient situated in said magnetic resonance scanner.

5. A method as claimed in claim 1 comprising explaining said maximum measurement time parameter, or a measurement time derived therefrom, at said input interface during said magnetic resonance data acquisition procedure.

6. A method as claimed in claim 1 comprising using said maximum time parameter to set a threshold value that is as a warning that indicates that said threshold is exceeded.

7. A method as claimed in claim 1 comprising manually changing said recording parameters via said input interface during said measurement procedure, and automatically determining, in said control computer, an energy input into the patient that has already occurred at a time when each change is made, and updating said maximum measurement time parameter dependent on the calculated energy input.

8. A method as claimed in claim 1 comprising calculating said energy input dependent on radio-frequency (RF) pulses that are radiated in said magnetic resonance sequences, by affirming respective energy associated with each RF pulse, to obtain a sum, and comparing said sum with a further threshold value that is derived from said maximum of said measurement time.

9. A method as claimed in claim 8 comprising establishing the energy input associated with each RF pulse by identifying a flip angle that is produced by a respective RF pulse and applying a known relationship between an RF transmitter voltage and said flip angle to determine the respective energy input associated with the respective RF pulse.

10. A method as claimed in claim 9 comprising establishing said relationship from a prior measurement provided to said control computer, or from a worst-case assumption algorithm executed by said control computer.

11. A method as claimed in claim 9 comprising determining the energy input to the patient by also taking into account an absorption value of the patient, from the calculated input energy for a respective RF pulse and the flip angle produced by that respective RF pulse.

12. A method as claimed in claim 11 comprising reading said absorption value from a characteristic field.

13. A method as claimed in claim 11 comprising determining said absorption value dependent on at least one of patient data, a worst-case assumption algorithm, and a tissue absorption model.

14. A method as claimed in claim 1 comprising establishing a maximum energy input that is imparted to the patient as said measurement sequence after each updating of a recording parameter or as part of a routinely implemented sequence check in said control computer.

15. A method as claimed in claim 1 comprising determining said maximum measurement time parameter as a maximum possible measurement duration for a maximum possible number of individual repetitions of an identical magnetic resonance sequence.

16. A magnetic resonance apparatus comprising:
a magnetic resonance scanner;
a control computer configured to operate said magnetic resonance scanner, while a patient is situated therein, to execute a magnetic resonance data acquisition procedure comprising a plurality of individual magnetic resonance sequences that are executed sequentially;
said control computer being configured to establish a maximum human time parameter that designates a maximum possible measurement time for sequentially executing at least some of said magnetic resonance sequences in said plurality of magnetic sequences, before a threshold value is exceeded that designates an overall energy input into the patient during said magnetic resonance data acquisition procedure, said control computer establishing said maximum measurement time parameter dependent on known recording parameters for said magnetic resonance data acquisition procedure; and
said control computer comprising an input interface via which an operator makes manual entries of at least some of said recording parameters, and when an operator makes said manual entries of at least one of said recording parameters that do not restrict said measurement time, said control computer being configured to automatically limit a designation of said measurement time at said input interface to said maximum measurement time parameter, to generate control signals in said control computer representing said magnetic resonance data acquisition procedure with said measurement time limited to said maximum, in a form for forwarding to said magnetic resonance scanner.

17. A non-transitory, computer-readable data storage medium encoded with programming instructions, said storage medium being loaded into a control computer of a magnetic resonance apparatus, that also comprises a magnetic resonance scanner, and said programming instructions causing said control computer to:
operate a magnetic resonance scanner, while a patient is situated therein, to execute a magnetic resonance data acquisition procedure comprising a plurality of individual magnetic resonance sequences that are executed sequentially;
establish a maximum human time parameter that designates a maximum possible measurement time for sequentially executing at least some of said magnetic resonance sequences in said plurality of magnetic sequences, before a threshold value is exceeded that designates an overall energy input into the patient during said magnetic resonance data acquisition procedure, said control computer establishing said maximum measurement time parameter dependent on known recording parameters for said magnetic resonance data acquisition procedure; and
when an operator makes manual entries, via an input interface of said control computer, that do not restrict said measurement time, automatically limit a designation of said measurement time at said input interface to said maximum measurement time parameter, and generate control signals in said control computer representing said magnetic resonance data acquisition procedure with said measurement time limited to said maximum, in a form for forwarding to said magnetic resonance scanner.

* * * * *